(12) United States Patent
Fujimori et al.

(10) Patent No.: US 10,015,375 B2
(45) Date of Patent: Jul. 3, 2018

(54) IMAGE PICKUP APPARATUS AND ENDOSCOPE INCLUDING THE SAME

(71) Applicant: OLYMPUS CORPORATION, Tokyo (JP)

(72) Inventors: Noriyuki Fujimori, Suwa (JP); Takatoshi Igarashi, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 345 days.

(21) Appl. No.: 14/676,045

(22) Filed: Apr. 1, 2015

(65) Prior Publication Data
US 2015/0207965 A1    Jul. 23, 2015

Related U.S. Application Data

(63) Continuation of application No. PCT/JP2013/075140, filed on Sep. 18, 2013.

(30) Foreign Application Priority Data

Oct. 5, 2012  (JP) .................................. 2012-223412

(51) Int. Cl.
*A62B 1/04* (2006.01)
*H04N 5/225* (2006.01)
*H01L 27/146* (2006.01)
*A61B 1/05* (2006.01)

(52) U.S. Cl.
CPC ........... *H04N 5/2251* (2013.01); *A61B 1/051* (2013.01); *H01L 27/14618* (2013.01); (Continued)

(58) Field of Classification Search
CPC .............. A61B 1/051; H01L 27/14618; H01L 2224/16225; H01L 2224/45144;
(Continued)

(56) References Cited

U.S. PATENT DOCUMENTS

2004/0130640 A1 * 7/2004 Fujimori ............... H01L 23/481
348/294
2012/0220826 A1    8/2012 Yamamoto
(Continued)

FOREIGN PATENT DOCUMENTS

EP    1577950 A1    9/2005
EP    2 614 767 A1    7/2013
(Continued)

OTHER PUBLICATIONS

Extended Supplementary European Search Report dated Apr. 20, 2016 in related European Application No. 13 84 4384.1.
(Continued)

*Primary Examiner* — Sathyanaraya V Perungavoor
*Assistant Examiner* — Peet Dhillon
(74) *Attorney, Agent, or Firm* — Scully, Scott, Murphy & Presser, P.C.

(57) ABSTRACT

An image pickup device including a vacant space portion that allows a connection electrode to be exposed to a second main surface side, the vacant space portion being formed at a position overlapping at least the connection electrode in a state where the image pickup device is viewed in plan view from a thickness direction A, and the connection electrode exposed to the second main surface side is electrically connected with a substrate at a position in the vacant space portion, the position overlapping the image pickup device in the state where the image pickup device is viewed in plan view from the thickness direction.

11 Claims, 10 Drawing Sheets

(52) U.S. Cl.
CPC . *H04N 5/2253* (2013.01); *H01L 2224/16225* (2013.01); *H01L 2224/45144* (2013.01); *H01L 2224/48091* (2013.01); *H04N 2005/2255* (2013.01)

(58) Field of Classification Search
CPC ........ H01L 2224/48091; H04N 5/2253; H04N 2005/2255
See application file for complete search history.

(56) References Cited

U.S. PATENT DOCUMENTS

| | | | |
|---|---|---|---|
| 2013/0314521 | A1 | 11/2013 | Satake et al. |
| 2014/0063501 | A1* | 3/2014 | Hirokubo ............... G02B 5/284 356/416 |

FOREIGN PATENT DOCUMENTS

| | | |
|---|---|---|
| JP | 2004-207461 A | 7/2004 |
| JP | 2005-175293 A | 6/2005 |
| JP | 2008-118568 A | 5/2008 |
| JP | 2009-016623 A | 1/2009 |
| JP | 2009-296542 A | 12/2009 |
| JP | 2011-147091 A | 7/2011 |
| WO | WO 2004/059740 A1 | 7/2004 |
| WO | 2012/032935 A1 | 3/2012 |
| WO | 2012/120734 A1 | 9/2012 |

OTHER PUBLICATIONS

International Search Report dated Nov. 5, 2013 issued in PCT/JP2013/075140.

* cited by examiner

IMAGE PICKUP APPARATUS AND ENDOSCOPE INCLUDING THE SAME

CROSS REFERENCE TO RELATED APPLICATION

This application is a continuation application of PCT/JP2013/075140 filed on Sep. 18, 2013 and claims benefit of Japanese Application No. 2012-223412 filed in Japan on Oct. 5, 2012, the entire contents of which are incorporated herein by this reference.

BACKGROUND OF THE INVENTION

1. Field of the Invention

The present invention relates to an image pickup apparatus provided with an image pickup device including on a first main surface thereof a light-receiving portion and a connection electrode configured to be connected to an external apparatus, and an endoscope including the image pickup apparatus.

2. Description of the Related Art

Conventionally, electronic instruments have been well-known such as an electronic endoscope, a mobile phone with camera, a digital camera, and the like which are provided with an image pickup apparatus including an image pickup device such as CCD, CMOS.

An image pickup apparatus generally includes a solid-state image pickup device (hereinafter, simply referred to as image pickup device) having on a distal end surface as a first main surface thereof a light-receiving portion, and a cover glass stuck on the distal end surface of the image pickup device, for protecting the light-receiving portion. In addition, a configuration of an image pickup apparatus is well-known, in which distal ends of inner leads extended from a flexible substrate (hereinafter, simply referred to as substrate) on which electronic components such as a capacitor, a resistor, and a transistor are mounted are electrically connected to a plurality of bonding pads as connection electrodes provided on the distal end surface of the image pickup device and configured to be connected to an external apparatus.

Note that a signal cable is electrically connected to the substrate, and thereby an electric signal of the image of the region to be examined, light therefrom having been received at the light-receiving portion of the image pickup device, is transmitted to external apparatuses such as an image processing apparatus, a monitor, and the like, through the substrate and the signal cable.

In addition, for the purpose of size reduction of an image pickup apparatus, a substrate is generally configured to be located at a position more rearward than a rear end surface of the image pickup device, the rear end surface being a second main surface opposite to the distal end surface of the image pickup device.

Therefore, inner leads and a substrate are generally configured such that the distal ends of the inner leads are electrically connected to a plurality of bonding pads provided on the distal end surface of the image pickup device, and thereafter the substrate is bent along the bottom surface or side surface of the image pickup device to be extended more rearward than the image pickup device, and such a configuration is disclosed in Japanese Patent Application Laid-Open Publication No. 2005-175293, for example.

SUMMARY OF THE INVENTION

An image pickup apparatus according to one aspect of the present invention is an image pickup apparatus which includes an image pickup device including on a first main surface thereof a light-receiving portion and a connection electrode to be connected to an external apparatus, and the image pickup apparatus includes: a vacant space portion that allows the connection electrode to be exposed to a second main surface side, the vacant space portion being formed on the image pickup device at a position overlapping at least the connection electrode in a state where the image pickup device is viewed in plan view from a thickness direction of the image pickup device, the thickness direction connecting the first main surface and the second main surface which is opposite to the first main surface, wherein the connection electrode exposed to the second main surface side is electrically connected with a substrate at a position in the vacant space portion, the position overlapping the image pickup device in the state where the image pickup device is viewed in plan view from the thickness direction.

In addition, an endoscope including an image pickup apparatus according to one aspect of the present invention is provided with the image pickup apparatus according to any one of claims 1 to 8.

DETAILED DESCRIPTION OF THE PREFERRED EMBODIMENTS

Hereinafter, an embodiment of the present invention will be described with reference to drawings. Note that each of the drawings is a pattern diagram, and care should be taken to the fact that the relationship between the thicknesses and widths of the respective members, a ratio of the thickness of a certain member to that of another member, and the like are different from the actual ones. It is needless to say that the drawings include a part in which a relationship and ratio among the dimensions are different from those in other drawings.

Figure 1:
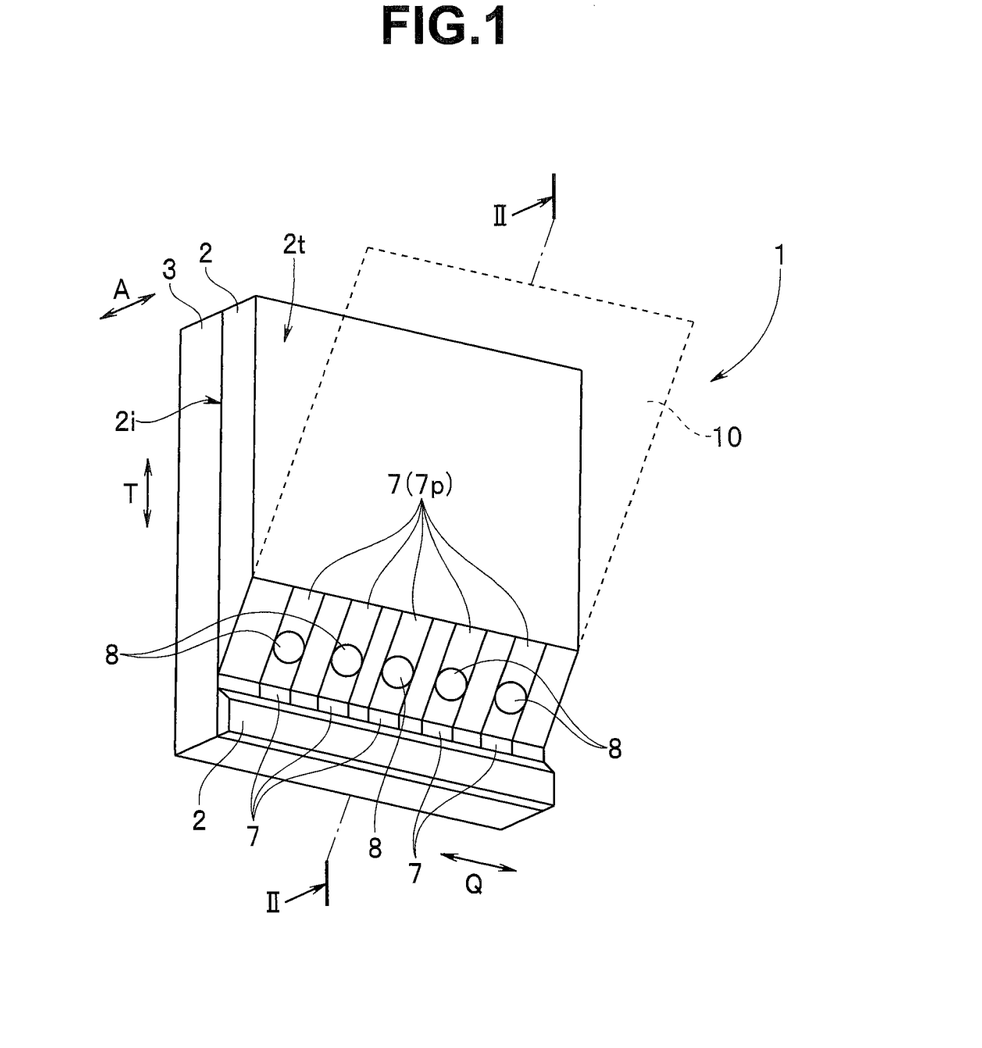
FIG. 1 is a perspective view schematically showing a configuration of an image pickup apparatus according to a present embodiment.
Figure 2:
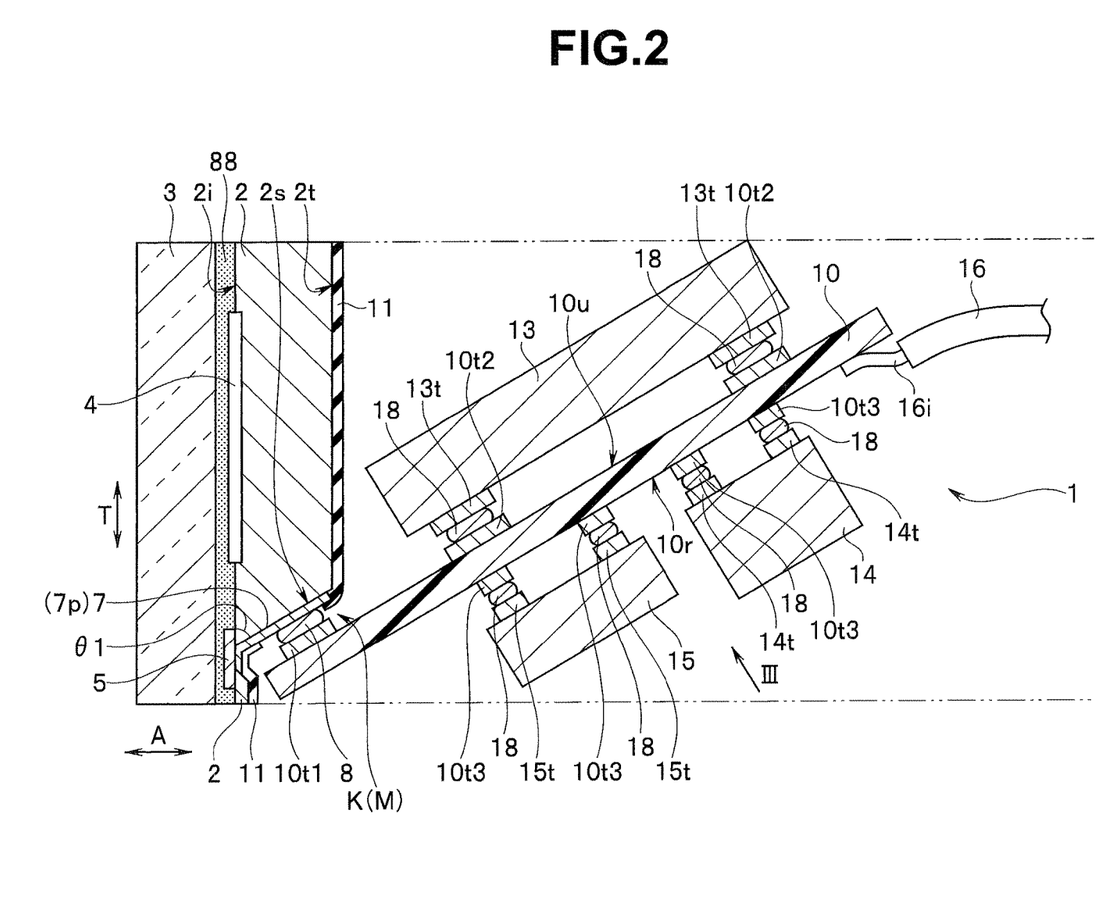
FIG. 2 is a cross-sectional view of the image pickup apparatus taken along II-II line in FIG. 1.
Figure 3:
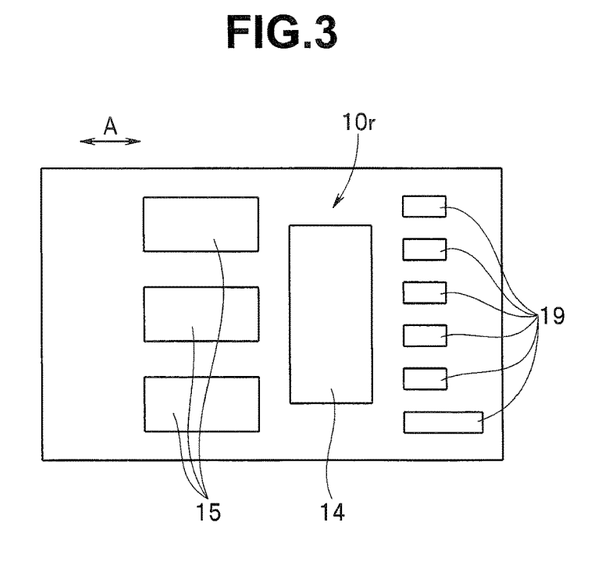
FIG. 3 is a plan view of a substrate in FIG. 2, viewed from a direction indicated by the sign III in FIG. 2.

FIG. 1 is a perspective view schematically showing a configuration of an image pickup apparatus according to a present embodiment; FIG. 2 is a cross-sectional view of the image pickup apparatus taken along the II-II line in FIG. 1; and FIG. 3 is a plan view of the substrate in FIG. 2, viewed from a direction indicated by the sign III in FIG. 2.

As shown in FIGS. 1 and 2, an image pickup apparatus 1 includes an image pickup device 2 which has a light-receiving portion 4 formed at a substantially center portion of a distal end surface 2i as a first main surface and a plurality of bonding pads 5, which are connection electrodes configured to be connected to external apparatuses, formed at a peripheral portion of the light-receiving portion 4 on the distal end surface 2i.

Note that the plurality of bonding pads 5 are formed on the distal end surface 2i along a width direction Q of the image pickup device 2 at positions lower than the light-receiving portion 4, for example, in a height direction T of the image pickup device 2 which is perpendicular to a thickness direction A of the image pickup device 2. In addition, the thickness direction A is a direction which connects the distal end surface 2i of the image pickup device 2 and a rear end surface 2t as a second main surface which is opposite to the distal end surface 2i. Furthermore, the width direction Q is a direction perpendicular to the thickness direction A and the height direction T.

In addition, a cover glass 3 that protects the light-receiving portion 4 is stuck to the distal end surface 2i through a bonding layer 88 made of transparent adhesive or the like. Note that the cover glass 3 is formed so as to have an outer shape same as that of the image pickup device 2, or smaller than that of the image pickup device 2 and larger than the light-receiving portion 4.

That is, when the image pickup device 2 is viewed in plan view from the thickness direction A after the cover glass 3 is stuck to the distal end surface 2i, the entirety of the outer shape of the cover glass 3 overlaps at least the light-receiving portion 4, and also the image pickup device 2. In other words, when the image pickup device 2 is viewed in plan view from the thickness direction A after the cover glass is stuck to the distal end surface 2i, the outer shape of the cover glass 3 does not protrude outside the outer shape of the image pickup device 2.

In addition, on the rear end surface 2t of the image pickup device 2, a protective film 11 for protecting the rear end surface 2t is formed.

Furthermore, a cutout K as a vacant space portion M for allowing the plurality of bonding pads 5 to be exposed to the rear end surface 2t side is formed on the image pickup device 2 at a position overlapping at least the plurality of bonding pads 5 when the image pickup device 2 is viewed in plan view from the thickness direction A.

Specifically, the cutout K is formed in the size and shape which allow all of the plurality of bonding pads 5 to be exposed at once to the rear end surface 2t side, by cutting out the position overlapping at least the plurality of bonding pads 5 in the state where the image pickup device 2 is viewed in plan view from the thickness direction A, together with the lower end surface located on the lower side in the height direction T (hereinafter, simply referred to as lower side) of the image pickup device 2 and the both end surfaces in the width direction Q of the image pickup device 2. In addition, by forming the cutout K, only the position of the image pickup device 2 which overlaps the plurality of bonding pads 5 is penetrated in the thickness direction A.

Note that the cutout K is formed by chemical or physical etching, or mechanical grinding, etc.

In addition, an inclined end surface 2s which is inclined at a set angle θ1 with respect to the distal end surface 2i is formed on the image pickup device 2 by forming the cutout K. Note that the inclined angle of the inclined end surface 2s forms an acute angle.

In the case where a substrate constituting the image pickup device 2 is made of silicon, for example, if the cutout K is formed by wet etching, the cutout K is formed along the silicon crystal plane orientation, thereby allowing the inclined end surface 2s to be formed so as to be inclined at the set angle θ1 with respect to the distal end surface 2i. Note that, regarding a formation method of the vacant space portion M by the TSV (Through-Silicon Via), it is requested to refer to Japanese Patent Application Laid-Open Publication No. 2009-016623 filed by the applicant of the present invention, for example.

In the present embodiment, the plurality of bonding pads 5 exposed to the rear end surface 2t side by the cutout K are electrically connected with a substrate 10 at a position in the cutout K, the position overlapping the image pickup device 2 in the state where the image pickup device 2 is viewed in plan view from the thickness direction A.

Specifically, as shown in FIG. 2, wirings 7, which are extended from the plurality of bonding pads 5 by being electrically connected to the plurality of bonding pads 5 exposed to the rear end surface 2t side by the cutout K, are drawn out to the inclined end surface 2s formed by the cutout K of the image pickup device 2. In addition, connection electrodes 10t1, which are provided on a top surface 10u of the substrate 10 at positions on the distal end side in the thickness direction A (hereinafter, simply referred to as distal end side), are electrically connected to bevel pads 7p formed on the wirings 7 located on the inclined end surface 2s, through bumps 8.

Note that the bumps 8 may be either stud bumps or plated bumps. In addition, the protective film 11 is also formed on exposed portions of the wirings 7 which are located at positions other than the inclined end surface 2s and on a portion of the rear end surface 2t of the image pickup device 2, which is remained on the lower side of the image pickup device 2 after forming the cutout K.

The method of connecting the connection electrodes 10t1 to the bevel pads 7p includes: a method of forming each bump 8 on each bevel pad 7p after inclining the image pickup device 2 at set angle θ1 such that the inclined end surface 2s becomes parallel to the thickness direction A and then electrically connecting each connection electrode 10t1 to each bump 8, while maintaining the inclined state of the image pickup device 2, or by cancelling the inclined state of the image pickup device 2 and inclining the substrate 10 at the set angle θ1; a method of forming each bump 8 on each connection electrode 10θ and then inclining the image pickup device 2 at set angle θ1 such that the inclined end surface 2s becomes parallel to the thickness direction A, to electrically connect each bump 8 to each bevel pad 7p; or other methods.

Note that the electrical connection of the connection electrodes 10t1 to the bevel pads 7p is performed before injecting sealing resin 80 into a frame body 60 shown in FIG. 12 to be described later.

After the electrical connection of the connection electrodes 10t1 to the bevel pads 7p through the bumps 8, the substrate 10 is located at a rear side in the thickness direction A (hereinafter, simply referred to as rear side) of the image pickup device 2, in the state inclined at substantially the same or the same angle as the set angle θ1 of the inclined end surface 2s with respect to the distal end surface 2i and in a non-bent state, as shown in FIG. 2.

In addition, at a position more rearward than the image pickup device 2, connection electrodes 13t of electronic components 13, each of which is defined as another component, are electrically connected to connection electrodes 10t2 formed on the top surface 10u of the substrate 10, through bumps 18.

Furthermore, at a position more rearward than the image pickup device 2, connection electrodes 14t, 15t of electronic components 14, 15, each of which is defined as another component, are electrically connected to connection electrodes 10t3 formed on a bottom surface 10r, through bumps 18. Note that the electronic components 13 to 15 are a capacitor, a resistor, and a transistor, for example. The electronic components 13 to 15 may be connected to the connection electrodes 10t3 by soldering.

Furthermore, a plurality of connection electrodes 19 are formed on the bottom surface 10r of the substrate 10 at positions more rearward than the electronic component 14, as shown in FIG. 3, and the plurality of connection electrodes 19 are electrically connected with distal ends of a plurality of lead wires 16i extended from a signal cable 16, which is defined as another component, as shown in FIG. 2.

According to such a configuration, an electric signal of the image of the region to be examined, light therefrom having been received at the light-receiving portion 4 of the image pickup device 2, is transmitted to external apparatuses of the image pickup device 2, such as an image processing apparatus, a monitor, and the like, through a plurality of bonding pads 5, the wirings 7, bumps 8, the substrate 10, and the signal cable 16.

Note that, as shown in FIG. 2, the substrate 10, the electronic components 13 to 15, and the signal cable 16, which are located at positions more rearward than the image pickup device 2, are located in an area in which an entirety of the substrate, etc. overlaps over the image pickup device 2 when the image pickup device 2 is viewed in plan view from the thickness direction, that is, located within a projected area.

Specifically, as shown in FIG. 2, the substrate 10, the electronic components 13 to 15, the signal cable 16 are located in a space shown by the two-dot-chain lines extended respectively from the upper end, lower end, right end and left end (right end and left end are not shown in FIG. 2) of the image pickup device 2 to the rear side in the thickness direction A.

Thus, the present embodiment shows that the cutout K formed on the image pickup device 2 allows the plurality of bonding pads 5 formed on the distal end surface 2i of the image pickup device 2 to be exposed to the rear end surface 2t side. In addition, the present embodiment shows that the substrate 10 is electrically connected with the bevel pads 7p of the wirings 7 which are drawn out to the inclined end surface 2s formed on the image pickup device 2 by forming the cutout K and which are electrically connected to the plurality of bonding pads 5.

According to such a configuration, when the substrate 10 is electrically connected to the plurality of bonding pads 5, unlike the conventional configuration, there is no need for bending the inner leads extended from the distal end of the substrate 10 and the distal end side of the substrate 10 along the bottom surface or side surface of the image pickup device 2. As a result, the substrate 10 is located so as not to protrude outside the outer shape of the image pickup device 2, which enables the size reduction of the image pickup apparatus 1.

In addition, it is not necessary to bend the substrate 10, which prevents damage such as breaking of the substrate 10 due to bending, and improves the assembling workability of the image pickup apparatus 1. As a result, the productivity of the image pickup apparatus 1 is improved.

Furthermore, in the present embodiment, the substrate 10 is electrically connected to the bevel pads 7p of the wirings 7, and thereafter located at the rear of the image pickup device 2, in the state inclined at substantially the same or the same angle as the set angle θ1 of the inclined end surface 2s with respect to the distal end surface 2i.

Furthermore, the substrate 10, the electronic components 13 to 15, and the signal cable 16, which are located at positions more rearward than the image pickup device 2, are located in the area in which the entirety of the substrate and etc. overlaps over the image pickup device 2 when the image pickup device 2 is viewed in plan view from the thickness direction.

According to such a configuration, the substrate 10 is arranged so as to be inclined at the angle θ1 with respect to the distal end surface 2i at the rear of the image pickup device 2, which enables the substrate 10, and the electronic components 13 to 15 and the signal cable 16 which are electrically connected to the substrate 10 to be located in the area in which the entirety of the substrate, etc. overlaps over the image pickup device 2 when the image pickup device 2 is viewed in plan view from the thickness direction.

Thus, since the substrate 10, the electronic components 13 to 15, and the signal cable 16 are located in the area in which the entirety of the substrate, etc. overlaps over the image pickup device 2 when the image pickup device 2 is viewed in plan view from the thickness direction, it is not necessary to bend the substrate 10 unlike the conventional configuration. According to such a configuration, the substrate 10 is not damaged, or broken due to bending, and in addition, the assembling workability of the image pickup apparatus 1 is improved, which results in the improved productivity of the image pickup apparatus 1.

Furthermore, the substrate 10, the electronic components 13 to 15, and the signal cable 16 do not protrude outside the outer shape of the image pickup device 2, which enables the size reduction of the image pickup apparatus 1.

As described above, it is possible to provide the image pickup apparatus 1, size of which can be reduced by allowing the substrate 10 electrically connected to the bonding pads 5 provided on the distal end surface 2i of the image pickup device 2 to be extended to the rear of the image pickup device 2 within the outer shape of the image pickup device 2, without a need for bending the substrate, and to provide the endoscope including the image pickup apparatus 1.

Figure 4:
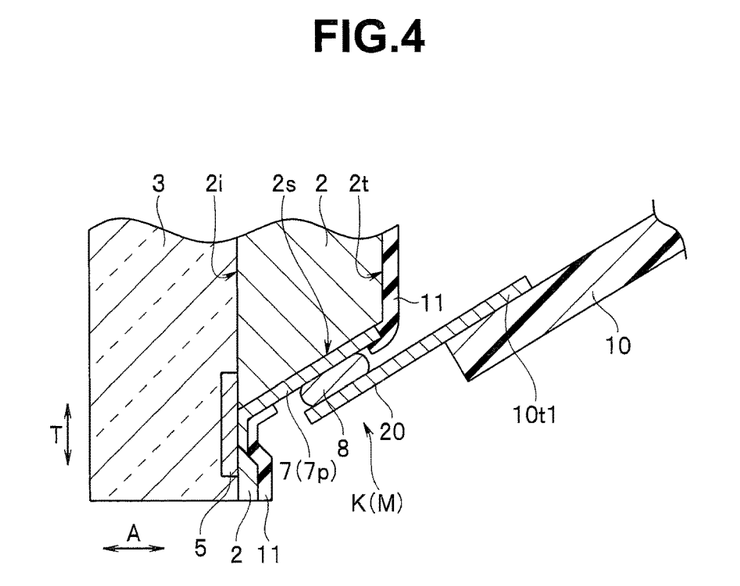
FIG. 4 is a partial cross-sectional view showing a configuration of a modified example in which an inner lead extended from the substrate is electrically connected to a bevel pad of a wiring in FIG. 2.

Note that a modified example is shown below with reference to FIG. 4. FIG. 4 is a partial cross-sectional view showing a configuration of a modified example in which the inner lead extended from the substrate is electrically connected to the bevel pad of the wiring in FIG. 2.

In the above-described present embodiment, the connection electrodes 10t1 of the substrate 10 are electrically connected, through the bumps 8, to the bevel pads 7p of the wirings 7 on the inclined end surface 2s, in the cutout K.

The configuration is not limited to the above-described configuration, and as shown in FIG. 4, an inner lead 20 as an extension electrode extended integrally from each of the connection electrodes 10t1 of the substrate 10 may be electrically connected to each of the bevel pads 7p on the inclined end surface 2s, through each of the bumps 8. Note that, also in this configuration, the substrate 10 is located at the rear side in the thickness direction A of the image pickup device 2 in the state inclined at the inclined angle θ1 with respect to the distal end surface 2i.

Figure 5:
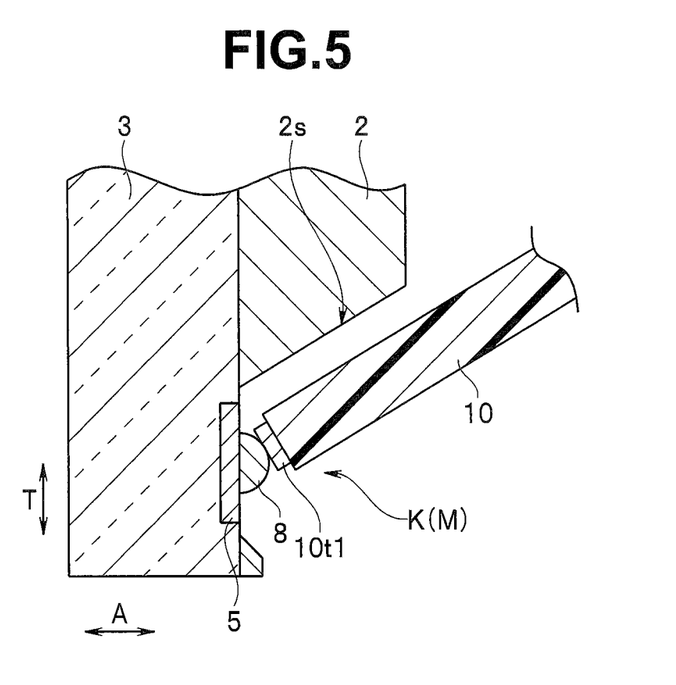
FIG. 5 is a partial cross-sectional view showing a configuration of a modified example in which the substrate in FIG. 2 is electrically and directly connected to a plurality of bonding pads exposed by a cutout to a rear end surface side of the image pickup device.

In addition, another modified example is shown with reference to FIG. 5. FIG. 5 is a partial cross-sectional view showing a configuration of a modified example in which the substrate in FIG. 2 is electrically and directly connected to a plurality of bonding pads exposed by the cutout to a rear end surface side of the image pickup device.

The above-described present embodiment shows that the connection electrodes 10t1 of the substrate 10 are electrically connected, through the bumps 8, to the bevel pads 7p of the wirings 7 drawn out to the inclined end surface 2s formed by the cutout K of the image pickup device 2.

The configuration is not limited to the above-described one, and as shown in FIG. 5, each of the connection electrodes 100 of the substrate 10 may be electrically and directly connected to each of the plurality of bonding pads 5 exposed to the rear end surface 2t side by the cutout K, through each of the bumps 8. Note that, also in this configuration, the substrate 10 is located at the rear side in the thickness direction A of the image pickup device 2 so as to have the inclined angle θ1 with respect to the distal end surface 2i.

Figure 6:
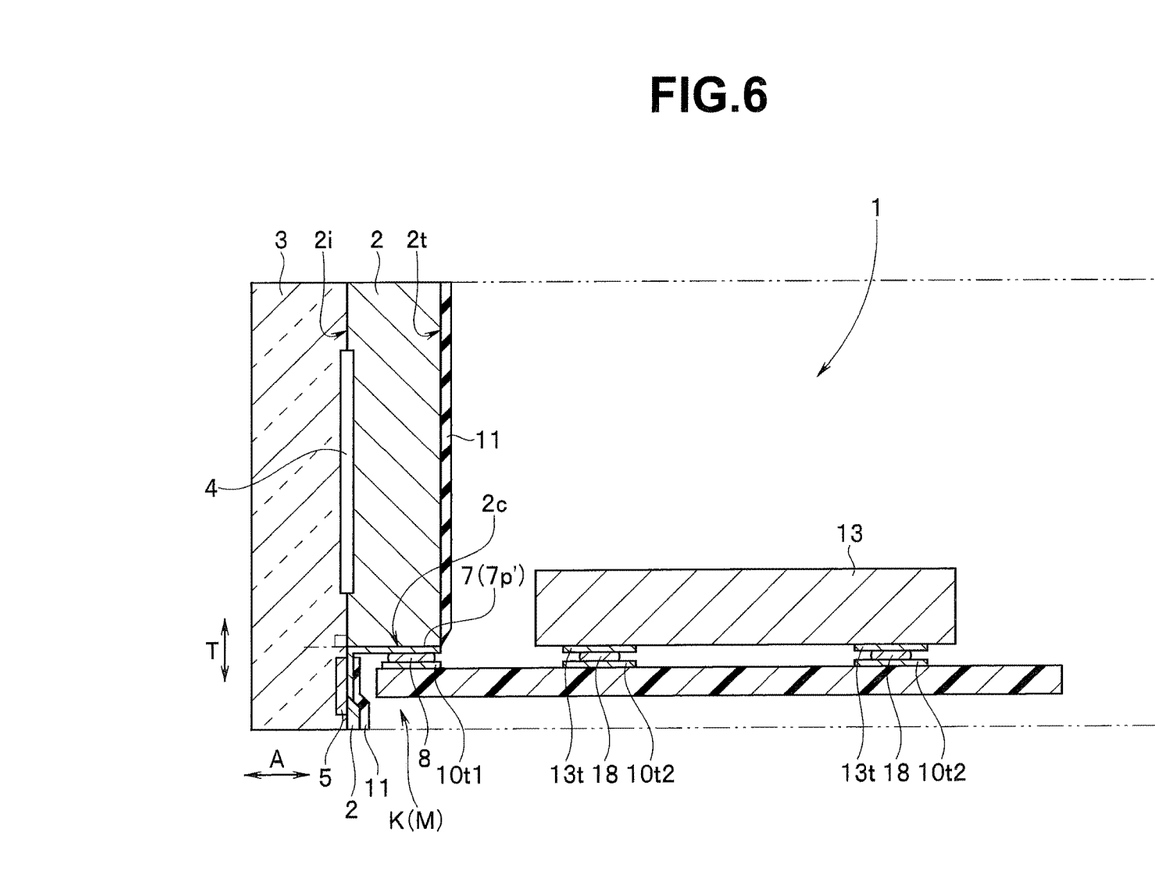
FIG. 6 is a partial cross-sectional view showing a configuration of a modified example in which an end surface formed by the cutout of the image pickup device in FIG. 2 is formed vertically with respect to a distal end surface of the image pickup device.

Furthermore, another modified example will be described with reference to FIG. 6. FIG. 6 is a partial cross-sectional view showing a configuration of a modified example in which the end surface formed by the cutout of the image pickup device in FIG. 2 is formed vertically with respect to the distal end surface of the image pickup device.

The above-described present embodiment shows that the end surface formed on the image pickup device 2 by the cutout K is the inclined end surface 2s inclined at the set angle θ1 with respect to the distal end surface 2i.

The configuration of the end surface is not limited thereto, and the end surface formed on the image pickup device 2 by the cutout K may be formed as a vertical end surface 2c which is vertical with respect to the distal end surface 2i, as shown in FIG. 6.

Note that, in this configuration, the wirings 7 extended by being electrically connected to the plurality of bonding pads 5 are drawn out to the vertical end surface 2c. In addition, the connection electrodes 10t1 of the substrate 10 are electrically connected, through the bumps 8, to pads 7p' of the wirings 7 drawn out to the vertical end surface 2c.

In addition, in the configuration shown in FIG. 6, the substrate 10 in the non-bent state is configured such that the connection electrodes 10t1 are electrically connected to the pads 7p' of the wirings 7 drawn out to the vertical end surface 2c. Therefore, the substrate 10 is located at the rear side in the thickness direction A of the image pickup device 2 so as to be substantially parallel or parallel to the vertical end surface 2c, that is, located so as to be vertical with respect to the distal end surface 2i, which allows the entirety of the substrate 10 to overlap over the image pickup device 2 when the image pickup device 2 is viewed in plan view from the thickness direction A.

Note that, in the configuration shown in FIG. 6, the electronic components 14, 15 are not connected to the bottom surface 10r of the substrate 10 so as to prevent the electronic components from protruding outside the outer shape of the image pickup device 2.

Furthermore, also in the configuration in which the vertical end surface 2c is formed on the image pickup device 2, the connection electrodes 10t1 may be electrically and directly connected to the plurality of bonding pads 5 exposed to the rear end surface 2t side, as shown in the above-described FIG. 5.

Figure 7:
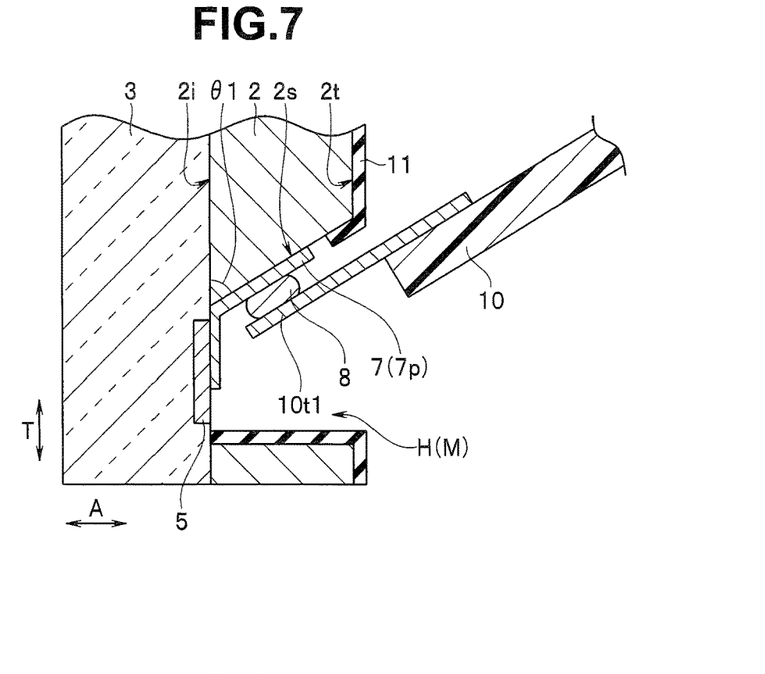
FIG. 7 is a partial cross-sectional view showing a modified example in which a vacant space portion for allowing the plurality of bonding pads in FIG. 2 to be exposed to the rear end surface side of the image pickup device is formed by an opening.
Figure 8:
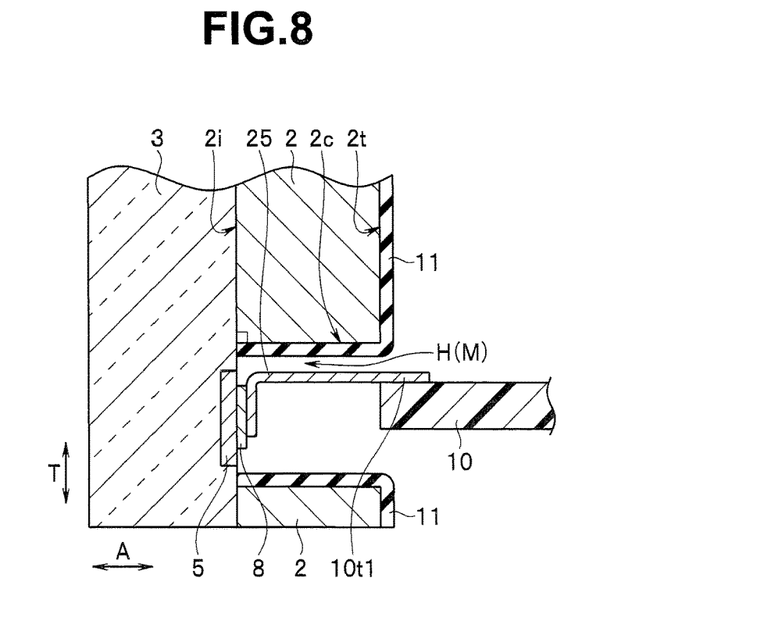
FIG. 8 is a partial cross-sectional view showing a configuration of a modified example in which the end surface, which is formed by the opening of the image pickup device in FIG. 7, is formed vertically with respect to the distal end surface of the image pickup device.

Hereinafter, other modified examples will be shown with reference to FIGS. 7 and 8. FIG. 7 is a partial cross-sectional view showing a modified example in which a vacant space portion for allowing the plurality of bonding pads in FIG. 2 to be exposed to the rear end surface side of the image pickup device is formed by an opening. FIG. 8 is a partial cross-sectional view showing a configuration of a modified example in which the end surface, which is formed by the opening of the image pickup device in FIG. 7, is formed vertically with respect to the distal end surface of the image pickup device.

In the above-described present embodiment, in the image pickup device 2, the vacant space portion M for allowing the plurality of bonding pads 5 to be exposed to the rear end surface 2t side at the position overlapping at least the plurality of bonding pads 5 when the image pickup device 2 is viewed in plan view from the thickness direction A is the cutout K.

The configuration of the vacant space portion is not limited thereto, and as shown in FIG. 7, in the image pickup device 2, the vacant space portion M may be an opening H configured by a through hole which penetrates the image pickup device 2 in the thickness direction A and which is formed at the position overlapping at least the plurality of bonding pads 5 when the image pickup device 2 is viewed in plan view from the thickness direction A, and the plurality of bonding pads 5 may be exposed to the rear end surface 2t side of the image pickup device 2 through the opening H.

Note that also the opening H is formed in the size and shape which allow all of the plurality of bonding pads 5 to be exposed at once to the rear end surface 2t side.

The opening H is also formed by chemical or physical etching, or mechanical grinding, etc.

Note that the formation of the opening H allows the inclined end surface 2s which is inclined at the set angle θ1 with respect to the distal end surface 2i to be formed on the image pickup device 2, similarly as in the configuration shown in FIG. 2. In addition, similarly as in the above-described present embodiment, the connection electrodes 100 of the substrate 10 are electrically connected, through the bumps 8, to the bevel pads 7p of the wirings 7 drawn out to the inclined end surface 2s, and after the connection, the substrate 10 is inclined at the set angle θ1 with respect to the distal end surface 2i at the rear of the image pickup device 2.

Furthermore, as shown in FIG. 8, the end surface formed on the image pickup device 2 by the opening H may be formed as the vertical end surface 2c which is vertical to the distal end surface 2i similarly in the configuration shown in FIG. 6.

In this case, the connection electrodes 10t1 of the substrate 10 are electrically connected to the bumps 8 provided on the plurality of bonding pads 5, through inner leads 25.

Also in the connection configuration shown in FIG. 8, after the connection, the substrate 10 is located vertically to the distal end surface 2i at the rear of the image pickup device 2, similarly as in the configuration shown in FIG. 6.

Furthermore, even in the case where the vacant space portion M is formed by the opening H, the connection electrodes 10t1 may be electrically and directly connected to the plurality of bonding pads 5 exposed to the rear end surface 2t side, as shown in FIG. 5.

Figure 9:
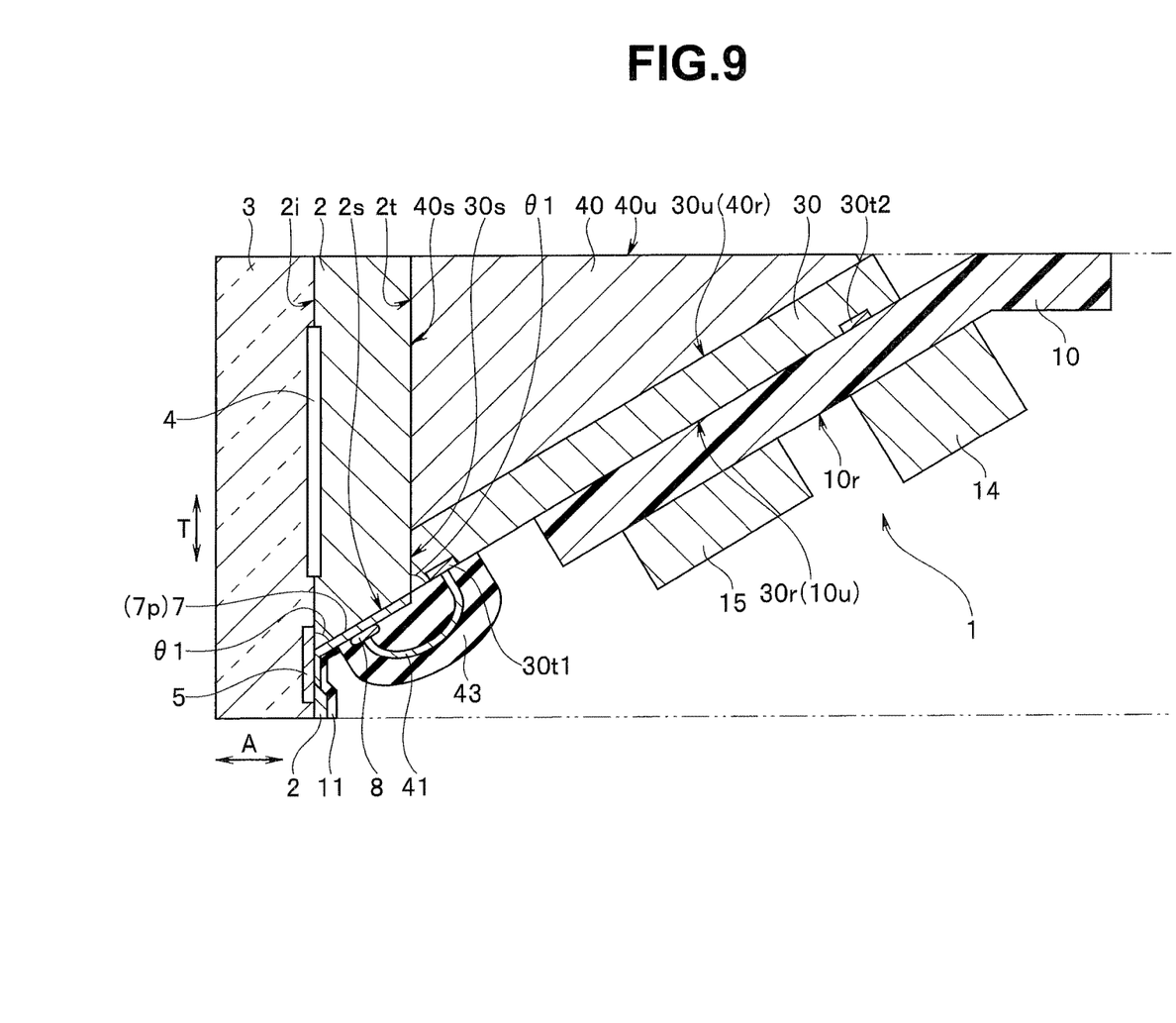
FIG. 9 is a partial cross-sectional view showing a modified example in which the substrate is electrically connected, through a processing circuit chip, to the bevel pad provided on the wiring of an inclined end surface of the image pickup device in FIG. 2.
Figure 10:
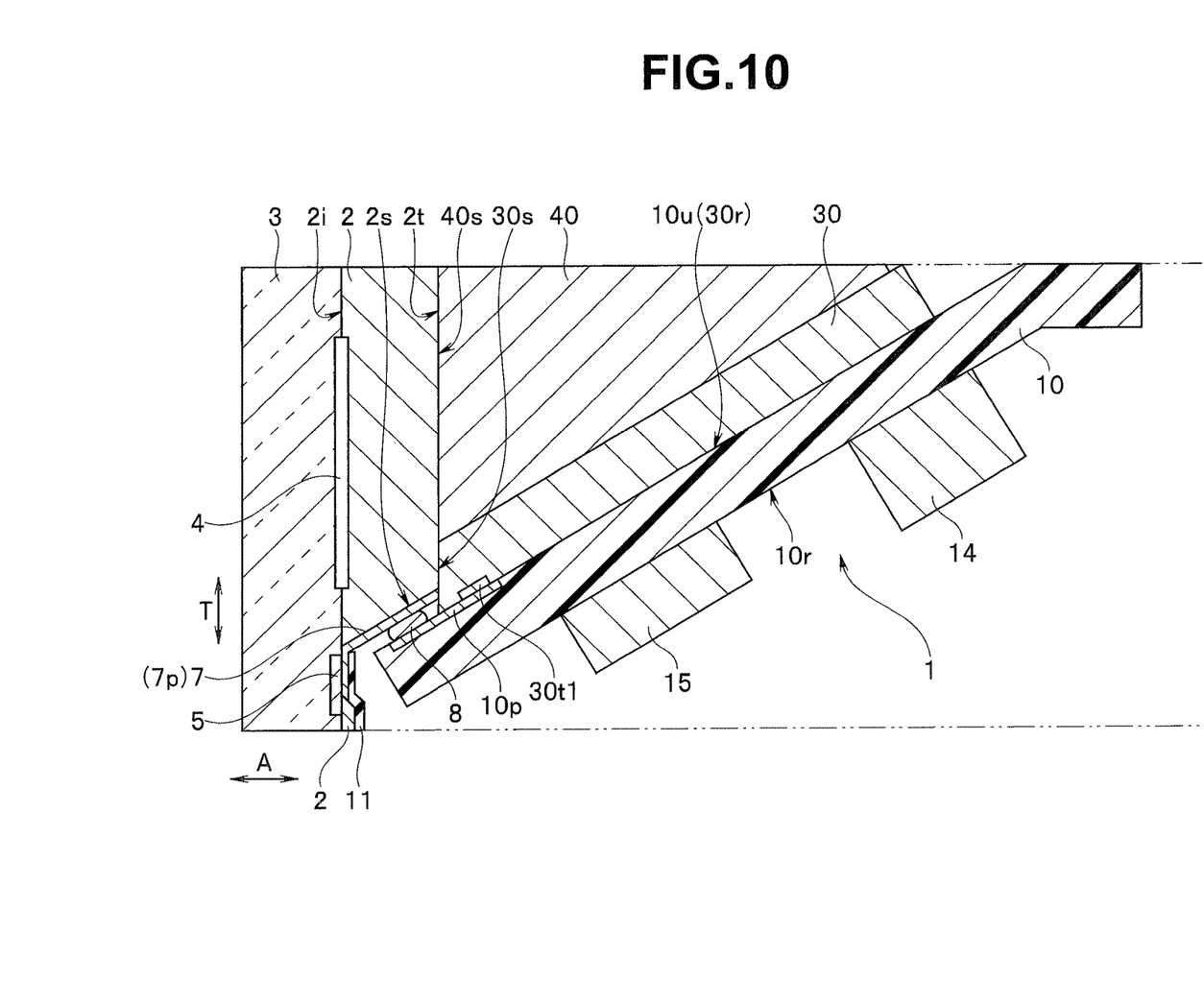
FIG. 10 is a partial cross-sectional view showing a modified example in which the substrate in FIG. 9 is electrically and directly connected to the bevel pad of the wiring drawn out to the inclined end surface of the image pickup device.

Hereinafter, other modified examples will be shown with reference to FIGS. 9 and 10. FIG. 9 is a partial cross-sectional view showing a modified example in which the substrate is electrically connected to the bevel pad provided to the wiring of the inclined end surface of the image pickup device in FIG. 2 through the processing circuit chip. FIG. 10 is a partial cross-sectional view showing a modified example in which the substrate in FIG. 9 is electrically and directly connected to the bevel pad of the wiring drawn out to the inclined end surface of the image pickup device.

As shown in FIG. 9, a distal end surface 30s of a processing circuit chip 30 defined as another member is fixed to the rear end surface 2t of the image pickup device 2 such that the processing circuit chip 30 is inclined at the set angle θ1 which is same as the inclined angle of the inclined end surface 2s and the bottom surface 30r is located parallel to the inclined surface 2s.

Note that a part of the bottom surface 30r of the processing circuit chip 30 is fixed to the top surface 10u at a position on the distal end side of the substrate 10. Furthermore, also in this configuration, the substrate 10 is located at the rear of the image pickup device 2 so as to be inclined at the set angle θ1 with respect to the distal end surface 2i. By forming the distal end surface 30s of the processing circuit chip 30 by wet etching similarly as the cutout K, the distal end surface 30s is formed along the silicon crystal plane orientation, and thereby enabling the distal end surface 30s to be formed so as to be inclined with respect to the inclined end surface 2s of the image pickup device at the angle θ1 which is parallel to the inclined angle of the inclined end surface 2s.

The processing circuit chip 30 performs various kinds of processing on the electric signal of the image of the region to be examined, light therefrom having been received at the light-receiving portion 4, and the processing circuit chip 30 is fixed to the top surface 10u of the substrate 10, to thereby fix the arranging position and the angle of the substrate 10.

Connection electrodes 30t1 are formed on the bottom surface 30r at positions on the distal end side of the processing circuit chip 30, and the connection electrodes 30t1 are electrically connected to the bumps 8 on the bevel pads 7p of the wirings 7 drawn out to the inclined end surface 2s of the image pickup device 2, through Au wires 41, for example. Note that the Au wires 41 are covered with insulating members 43 which prevents the Au wires 41 from being exposed.

In addition, connection electrodes 30t2 are formed on the bottom surface 30r at positions on the proximal end side of the processing circuit chip 30, and the connection electrodes 30t2 are electrically connected with connection electrodes, not shown, provided on the top surface 10u of the substrate 10. Note that the electronic components 14, 15 are electrically connected to the bottom surface 10r of the substrate 10.

Furthermore, on the upper side of the processing circuit chip 30 in the height direction T (hereinafter, just referred to as upper side), a heat radiation supporting member 40, which is defined as another member, is provided, the heat radiation supporting member 40 having a distal end surface 40s which is fixed to the rear end surface 2t of the image pickup device 2 and a bottom surface 40r which is inclined at the angle θ1 same as the inclined angle of the top surface 30u of the processing circuit chip 30 and fixed on the top surface 30u of the processing circuit chip 30.

Note that the heat radiation supporting member 40 is made of a member having high heat conductivity, such as brass, and formed in a size and a shape such that a top surface 40u does not protrude outside the outer shape of the image pickup device 2.

The heat radiation supporting member 40 has a function for releasing the heat of the image pickup device 2 to the substrate 10, through the processing circuit chip 30, and also has a function for supporting the processing circuit chip 30 which is fixed to the rear end surface 2t only with the distal end surface 30s.

Note that, as shown in FIG. 10, the substrate 10 may be configured such that the wiring patterns 10p provided on the distal end side of the top surface 10u of the substrate are electrically connected, through the bumps 8, to the bevel pads 7p of the wirings 7 drawn out to the inclined end surface 2s of the image pickup device 2.

In the configuration shown in FIG. 10, the connection electrodes 30t1, which are provided on the distal end side of the bottom surface 30r of the processing circuit chip 30, are electrically connected to the bevel pads 7p through the wiring patterns 10p.

In addition, also in the configuration as shown in FIG. 10, the substrate 10 is located at the rear side in the thickness direction A of the image pickup device 2 so as to be inclined at the set angle θ1 with respect to the distal end surface 2i.

Also in the configuration shown in FIGS. 9 and 10, the substrate 10, the processing circuit chip 30, the heat radiation supporting member 40, and the electronic components 14, 15 fixed to the substrate 10 are located at the rear side in the thickness direction A of the image pickup device 2 such that the entirety of these overlaps over the image pickup device 2 when the image pickup device 2 is viewed in plan view from the thickness direction A.

Such configurations shown in FIGS. 9 and 10 can also provide the same effects as those in the present embodiment, and provide the image pickup apparatus 1 that is capable of more effectively radiating the heat of the image pickup device 2 by providing the heat radiation supporting member 40.

As a matter of course, the vacant space portion M may be formed by the opening H in the configurations shown in FIGS. 9 and 10.

Figure 11:
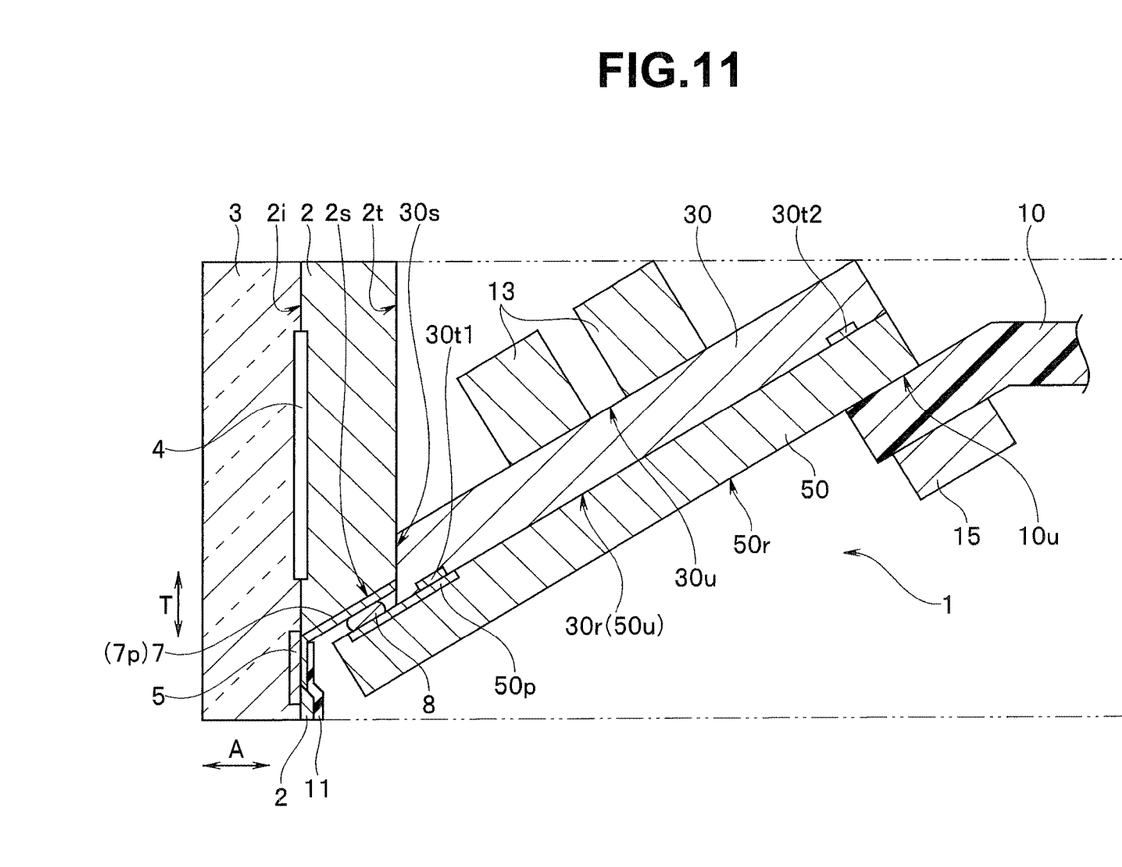
FIG. 11 is a partial cross-sectional view showing a modified example in which the substrate is electrically connected, through an interposer substrate, to the bevel pad of the wiring drawn out to the inclined end surface of the image pickup device.

Hereinafter, another modified example is shown with reference to FIG. 11. FIG. 11 is a partial cross-sectional view showing a modified example in which the substrate is electrically connected to the bevel pad of the wiring drawn out to the inclined end surface of the image pickup device through an interposer substrate.

As shown in FIG. 11, in the structure in which the distal end surface 30s of the processing circuit chip 30 is fixed to the rear end surface 2t of the image pickup device 2 similarly as in the configurations shown in FIGS. 9 and 10, a top surface 50u of a well-known interposer substrate 50 defined as another component is fixed to the bottom surface 30r of the processing circuit chip 30 so as to be inclined at the set angle θ1 with respect to the distal end surface 2i. In addition, the interposer substrate 50 and the processing circuit chip 30 are electrically connected to each other with the connection electrodes 30t1 and 30t2 which are respectively formed on the distal end side and the proximal end side of the bottom surface 30r of the processing circuit chip 30.

Note that the connection electrodes 30t1 are electrically connected to the wiring patterns 50p formed on the distal end side of the top surface of the interposer substrate 50, and the wiring patterns 50p are electrically connected to the bevel pads 7p of the wirings 7 drawn out to the inclined end surface 2s of the image pickup device 2. According to such a configuration, the processing circuit chip 30 is electrically connected to the bevel pads 7p through the interposer substrate 50.

In addition, a plurality of electronic components 13 are electrically connected to the top surface 30u of the processing circuit chip 30.

Furthermore, the proximal end side of the top surface 50r of the interposer substrate 50 is electrically connected with the distal end side of the top surface 10u of the substrate 10. According to such a configuration, the substrate 10 is electrically connected to the bevel pads 7p through the interposer substrate 50. Note that, also in the configuration shown in FIG. 11, the substrate 10 is located at the rear side in the thickness direction A of the image pickup device 2 so as to be inclined at the set angle θ1 with respect to the distal end surface 2i.

The interposer substrate 50 is electrically connected to the bevel pads 7p by narrowing the circuit pitch of the substrate 10.

Also in the configuration shown in FIG. 11, the substrate 10, the processing circuit chip 30, the interposer substrate 50, and the electronic component 15 electrically connected to the substrate 10 are located at the rear side of the image pickup device 2 such that the entirety of these overlaps over the image pickup device 2 when the image pickup device 2 is viewed in plan view from the thickness direction A.

Note that, since the interposer substrate 50 is configured by a rigid member made of silicon or the like, if the interposer substrate 50 is fixed to the processing circuit chip 30, there is no need for providing the heat radiation supporting member 40 which supports the processing circuit chip 30 as shown in FIGS. 9 and 10. As a result, a plurality of electronic components 13 can be provided on the top surface 30u of the processing circuit chip 30.

Other effects are the same as those in the configurations shown in FIGS. 9 and 10. As a matter of course, the vacant space portion M may be formed by the opening H in the configuration shown in FIG. 11.

Thus, the image pickup apparatus 1 described with reference to FIGS. 1 to 11 is used as an image pickup unit, together with an objective lens unit. FIG. 12 is a cross-sectional view schematically showing an example of an image pickup unit using the image pickup apparatus shown in FIGS. 1 and 2.

Figure 12:
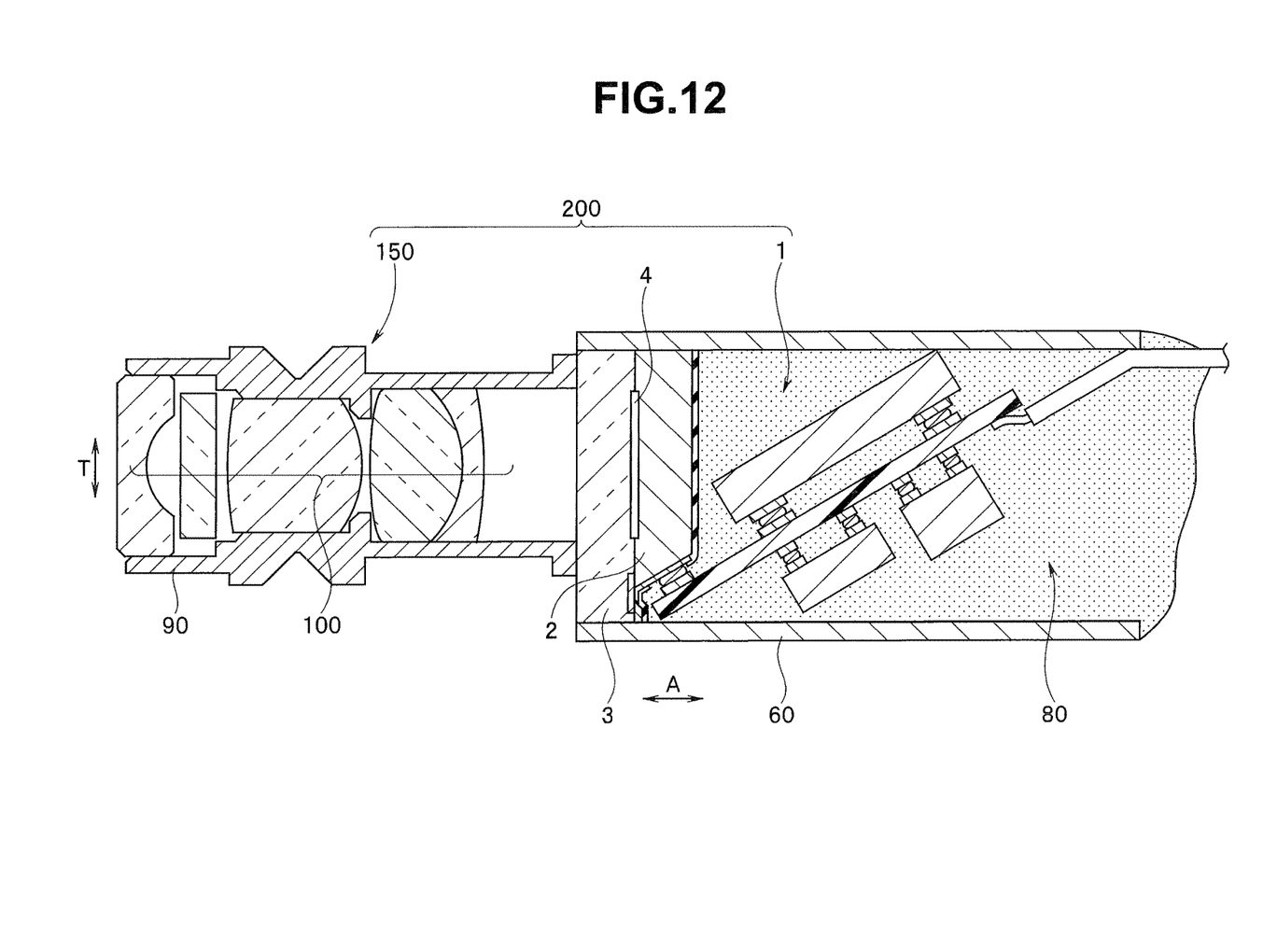
FIG. 12 is a cross-sectional view schematically showing an example of an image pickup unit using the image pickup apparatus shown in FIGS. 1 and 2.

As shown in FIG. 12, an image pickup unit 200 has a main portion configured by the image pickup apparatus 1 and an objective lens unit 150 located at the more front side in the thickness direction A than the image pickup apparatus 1.

The objective lens unit 150 is formed such that a plurality of lenses 100 are fixed to the inner peripheral surface of an objective lens frame 90 along the thickness direction A, and the rear end surface of the objective lens frame 90 in the thickness direction A is brought into contact with the area which is on the distal end surface of the cover glass 3 and which does not overlap the light-receiving portion 4.

In addition, the image pickup apparatus 1 is provided with a frame body 60 which covers the image pickup apparatus 1 on the outer peripheral surface of the cover glass 3 and image pickup device 2, and the sealing resin 80 is filled in the frame body 60.

According to such a configuration, the image pickup apparatus 1 has a necessary minimum outer shape which is substantially the same dimension as that of the outer shape of the image pickup device 2, which enables the size reduction of the image pickup apparatus.

It is needless to say that the image pickup unit 200 thus configured may be provided not only in medical or industrial endoscopes but also in medical capsule endoscope, for example, or may be applied to a mobile phone with a camera or a digital camera, not limited to the endoscopes.

What is claimed is:
1. An image pickup apparatus comprising:
an image pickup device having a first main surface and a second main surface on an opposite side of the first main surface, a light-receiving portion and a connection electrode are formed on the first main surface, the connection electrode having a front face and a rear face on an opposite side of the front face, the rear face abutting the first main surface;
a cover glass adhered to the first main surface of the image pickup device through a transparent bonding layer; and
a substrate electrically connected with the connection electrode,
wherein the image pickup device is provided with a vacant space portion, the vacant space portion being open to a second main surface side of the image pickup device, the front face of the connection electrode is covered by the bonding layer, the rear face of the connection electrode is exposed through the vacant space portion, and a distal end portion of the substrate inserted into the vacant space portion is electrically connected with the rear face of the connection electrode.

2. The image pickup apparatus according to claim 1, wherein
the vacant space portion is formed by an opening formed on the image pickup device along the thickness direction at the position overlapping at least the connection electrode in the state where the image pickup device is viewed in plan view from the thickness direction, and
the rear face of the connection electrode is exposed to the second main surface side through the opening.

3. The image pickup apparatus according to claim 1, wherein
the vacant space portion is formed by a cutout formed by cutting the position overlapping at least the connection electrode in the state where the image pickup device is viewed in plan view from the thickness direction and also cutting an end surface of the image pickup device in a direction perpendicular to the thickness direction, and
the rear face of connection electrode is exposed to the second main surface side through the cutout.

4. The image pickup apparatus according to claim 1, wherein
the substrate is electrically and directly connected to the connection electrode.

5. The image pickup apparatus according to claim 1, wherein
the substrate is electrically connected to the connection electrode through a wiring extended from the connection electrode.

6. The image pickup apparatus according to claim 5, wherein the substrate is electrically connected to the wiring extended to an end surface which is formed on the image pickup device by forming the vacant space portion and inclined at an acute angle with respect to the first main surface, or extended to an end surface which is formed on the image pickup device by forming the vacant space portion and perpendicular to the first main surface.

7. The image pickup apparatus according to claim 1, wherein
the substrate is electrically connected to the connection electrode through an extension electrode extended from the substrate.

8. The image pickup apparatus according to claim 1, wherein
the substrate is connected with another component, and the substrate and the other component are located so as to be away from the second main surface of the image pickup device in the thickness direction in such a manner that an entirety of the substrate and the other component overlaps over the image pickup device when the image pickup device is viewed in plan view from the thickness direction.

9. An endoscope comprising the image pickup apparatus according to claim 1.

10. The image pickup apparatus according to claim 1, wherein the vacant space portion is formed at a position where the vacant space portion overlaps the connection electrode when viewed in a plan view in a direction of thickness of the image pickup device, and the rear face of the connection electrode is exposed to the second main surface side by the vacant space portion.

11. The image pickup apparatus according to claim 1, wherein the vacant space portion is formed at a position where the vacant space portion overlaps the connection electrode when viewed in a plan view in a direction of thickness of the image pickup device, and the connection electrode and the substrate are electrically connected with each other in the vacant space portion.

* * * * *